United States Patent [19]

Fischer et al.

[11] 4,284,796
[45] Aug. 18, 1981

[54] PREPARATION OF 4-ACYLOXY-2-METHYL-CROTONALDEHYDES

[75] Inventors: Rolf Fischer, Heidelberg; Hans-Martin Weitz, Bad Durkheim, both of Fed. Rep. of Germany

[73] Assignee: BASF Aktiengesellschaft, Fed. Rep. of Germany

[21] Appl. No.: 78,722

[22] Filed: Sep. 25, 1979

[30] Foreign Application Priority Data

Oct. 16, 1978 [DE] Fed. Rep. of Germany ....... 2844949

[51] Int. Cl.³ .................. C07C 67/29; C07C 67/297; C07C 69/025; C07C 69/145; C07C 69/24
[52] U.S. Cl. ..................................... 560/262; 562/606; 562/607; 562/609
[58] Field of Search ............ 560/262, 410.9 N, 405.6, 560/602; 568/484

[56] References Cited

U.S. PATENT DOCUMENTS 3,639,437  2/1972  Fischer et al. ...................... 560/262

OTHER PUBLICATIONS

Chemische Berichte, 90, 1957, pp. 187–193.
Houben–Weyl, Methoden Der Organ. Chemie, vol. 5/1b, pp. 570–672.

*Primary Examiner*—Vivian Garner
*Attorney, Agent, or Firm*—Keil & Witherspoon

[57] ABSTRACT

A process for the preparation of a 4-acyloxy-2-methyl-crotonaldehyde of the formula

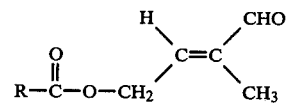

where R is hydrogen or an aliphatic radical of 1 to 5 carbon atoms, by reacting a 1,1,4-triacyloxy-2-methyl-but-2-ene of the formula

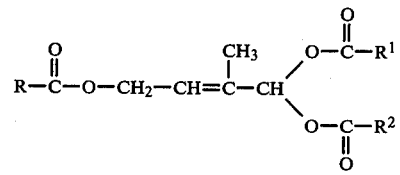

where $R^1$ and $R^2$ are each hydrogen or an aliphatic radical of 1 to 5 carbon atoms, with water in the presence of a carboxylic acid of the formula

R—COOH  III.

5 Claims, No Drawings

PREPARATION OF 4-ACYLOXY-2-METHYL-CROTONALDEHYDES

The present invention relates to a process for the preparation of a 4-acyloxy-2-methylcrotonaldehyde by reacting a 1,1,4-triacyloxy-2-methyl-but-2-ene with water in the presence of a carboxylic acid.

It is known that mixtures of (E)- and (Z)-4-acetoxy-crotonaldehyde are obtained when 1,1,4-triacetoxy-but-2-ene is refluxed with water, the reaction mixture is extracted with ether and the combined ether extracts are subjected to fractional distillation. The yield of 4-acetoxy-crotonaldehydes is only 40%. (Chemische Berichte, 90 (1957), 187–193).

It is an object of the present invention to prepare 4-acyloxy-2-methylcrotonaldehydes, which are suitable intermediates for the synthesis of derivatives of all-trans-vitamin A, from 1,1,4-triacyloxy-2-methyl-but-2-enes. It is a further objective to obtain, from isomer mixtures of an (E)- and (Z)-1,1,4-triacyloxy-2-methyl-but-2-ene, the (E)-isomer of the 4-acyloxy-2-methyl-crotonaldehyde in one reaction step, without an additional isomerization or separate stage, because only the latter is suitable for the preparation of the all-trans-vitamin A derivatives.

We have found that these objects are achieved and that a 4-acyloxy-2-methylcrotonaldehyde (4-acyloxy-2-methyl-but-2-en-1-al) of the formula

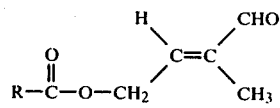

where R is hydrogen or an aliphatic radical of 1 to 5 carbon atoms is obtained in high yield, and virtually exclusively as a desired trans-isomer, if a 1,1,4-triacyloxy-2-methyl-but-2-ene of the formula

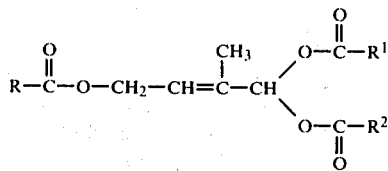

where $R^1$ and $R^2$ are each hydrogen or an aliphatic radical of 1 to 5 carbon atoms, is reacted with water in the presence of a carboxylic acid of the formula

R—COOH      III where R has the above meanings.

Where 4-acetoxy-2-methyl-crotonaldehyde (4-acetoxy-tiglicaldehyde) is prepared, the reaction can be represented by the following equation (—OAc-=—O—CO—CH$_3$):

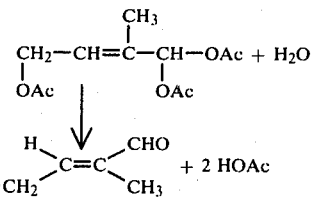

The outcome of the hydrolysis according to the invention, where the desired (E)-4-acyloxy-2-methylcrotonaldehyde is produced even from mixtures of (E)- and (Z)-1,1,4-triacyloxy-2-methyl-but-2-enes, is surprising, since it is known that specific cis-trans isomerizations can, in the majority of cases, only be carried out photochemically, in the presence of a free radical catalyst, such as nitric oxide or iodine, or in a few cases, thermally. (Houben-Weyl, Methoden der organischen Chemie, volume 5/lb, pages 670 to 672). The hydrolysis of mixtures of the (E)- and (Z)-isomers of the formula II would have been expected to give mixtures of (E)- and (Z)-4-acyloxy-2-methylcrotonaldehyde, and furthermore to have given much poorer yields.

A 1,1,4-triacyloxy-2-methyl-but-2-ene used as the starting material can be prepared, for example, by acyloxylating a 1-acyloxy-2-methyl-1,3-butadiene with a carboxylic acid and oxygen in the presence of a catalyst containing palladium and platinum. The ratio of the (E)-isomer to the (Z)-isomer is unimportant for the hydrolysis according to the invention since almost exclusively the desired (E)-4-acyloxy-2-methylcrotonaldehyde is obtained starting from the pure isomers or from mixtures in any ratio.

The radicals R, $R^1$ and $R^2$, which may be identical or different, are preferably hydrogen or alkyl of 1 to 5 carbon atoms, especially methyl, ethyl, propyl, n-butyl or i-butyl.

The reaction is carried out in the presence of a carboxylic acid of the formula III, where R has the above meanings. For economic and practical reasons, acetic acid is particularly preferred. The reaction is advantageously carried out in the presence of the carboxylic acid which is also used as the reactant and/or reaction medium in the preparation of the 1,1,4-triacyloxy-2-methyl-but-2-ene. By way of example, from 0.1 to 50 moles of carboxylic acid of the formula III are employed per mole of triacylate of the formula II.

The reaction is in general carried out at from 0° to 200° C., preferably from 80° to 200° C., under atmospheric or superatmospheric pressure, batchwise or continuously. The amount of water is advantageously from 1 to 50 moles, especially from 1 to 5 moles, per mole of starting material of the formula II.

The procedure employed is, for example, as follows: a mixture of the starting material of the formula II, water and the carboxylic acid of the formula III is brought to the reaction temperature and is kept thereat for from 1 to 5 hours. After distilling off carboxylic acids and excess water, the residue is fractionated to isolate the (E)-4-acyloxy-2-methylcrotonaldehyde.

The 4-acyloxy-2-methylcrotonaldehydes obtainable by the process of the invention are valuable starting materials for the preparation of terpenes. For example, (E)-4-acetoxy-2-methylcrotonaldehyde serves as a $C_5$-structural unit in the synthesis of vitamin A acetate.

In the Examples which follow, parts are by weight.

EXAMPLE 1

48.8 parts of 1,1,4-triacetoxy-2-methyl-but-2-ene, consisting, according to NMR analysis, of 46.4% of (E)-isomer and 53.6% of (Z)-isomer, are boiled with 500 parts of glacial acetic acid and 18 parts of water for 2.5 hours. After stripping off the acid and water on a rotary evaporator at from 40° to 50° C. under a waterpump vacuum, fractional distillation of the residue gives 23.2 parts of 4-acetoxy-2-methylcrotonaldehyde (81.6% of theory) of boiling point 102°–103° C./23.9 mbar ($n_D^{20}=1.4641$). According to NMR analysis (aldehyde protons), the aldehyde obtained consists of 98.0% (E)- and 2.0% (Z)-4-acetoxy-2-methylcrotonaldehyde.

EXAMPLE 2

48.8 parts of 1,1,4-triacetoxy-2-methyl-but-2-ene, having the isomer composition stated in Example 1, 400 parts of formic acid and 10.8 parts of water are boiled for 3 hours. After stripping off the formic acid and water on a rotary evaporator, fractional distillation of the residue gives 21.5 parts of 4-acetoxy-2-methylcrotonaldehyde (75.6% of theory) of boiling point 102°–105° C./21 mbar ($n_D^{20}=1.4642$). According to NMR analysis, the aldehyde obtained consists of 98.3% (E)- and 1.7% (Z)-4-acetoxy-2-methylcrotonaldehyde.

EXAMPLE 3

40.3 parts of 1,1,4-triacetoxy-2-methyl-but-2-ene having the isomer composition stated in Example 1, 80 parts of water and 12 parts of glacial acetic acid are refluxed for 3 hours.

After the solution has cooled, it is extracted with 50 parts by volume of ether, saturated with calcium chloride, and extracted three more times with 50 parts by volume of ether at a time. The combined ether extracts are dried with magnesium sulfate. After stripping off the ether, fractional distillation of the residue gives 18.8 parts of 4-acetoxy-2-methylcrotonaldehyde (80.1% of theory) of boiling point 100°–104° C./18.6 mbar ($n_D^{20}=1.4642$). Unconverted 1,1,4-triacetoxy-2-methyl-but-2-ene is not detectable. According to NMR analysis, the aldehyde obtained consists of 97.5% (E)- and 2.5% (Z)-4-acetoxy-2-methylcrotonaldehyde.

EXAMPLE 4

48.8 parts of 1,1,4-triacetoxy-2-methyl-but-2-ene, consisting, according to NMR analysis, of 75.5% (E)- and 24.5% (Z)-isomer, 250 parts of glacial acetic acid and 18 parts of water are boiled for 3 hours. After working up as described in Example 1, 23.9 parts of 4-acetoxy-2-methylcrotonaldehyde (84.1% of theory) of boiling point 92°–96° C./16 mbar ($n_D^{20}=1.4638$) are obtained. According to NMR analysis, the aldehyde obtained consists of 98,.5% (E)- and 1.5% (Z)-4-acetoxy-2-methylcrotonaldehyde.

COMPARATIVE EXAMPLE

Following the procedure described in Chem. Ber. 90 (1957), 192, Experiment 1, 40.3 parts of 1,1,4-triacetoxy-2-methyl-but-2-ene, consisting according to NMR analysis, of 46.4% (E)- and 53.6% (Z)-isomer, are boiled with 80 parts of water for 40 minutes. Analysis by gas chromatography of a sample of the organic phase which separates out even at the boil shows that only about 10% of the starting material has been converted to 4-acetoxy-2-methylcrotonaldehyde. The reaction mixture is boiled for a further 140 minutes. The solution, which is then homogeneous, is allowed to cool, extracted with 50 parts by volume of ether, saturated with calcium chloride and extracted three more times with 50 parts by volume of ether at a time. The combined ether extracts are dried with magnesium sulfate. After stripping off the ether, fractional distillation of the residue gives 12.6 parts of 4-acetoxy-2-methylcrotonaldehyde (53.8% of theory) of boiling point 103°–106° C./20 mbar ($n_D^{20}=1.4640$) and 9.1 parts of unconverted 1,1,4-triacetoxy-2-methyl-but-2-ene (22.6% of theory) of boiling point 118°–127° C./20 mbar ($n_D^{20}=1.4487$). According to NMR analysis, the aldehyde obtained consists of 89.3% (E)- and 10.7% (Z)-4-acetoxy-2-methylcrotonaldehyde.

We claim:

1. A process for the preparation of a 4-acyloxy-2-methylcrotonaldehyde of the formula

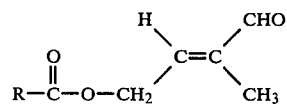

where R is hydrogen or an aliphatic radical of 1 to 5 carbon atoms, wherein a 1,1,4-triacyloxy-2-methyl-but-2-ene of the formula

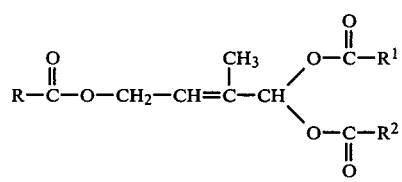

where R, $R^1$ and $R^2$ are each hydrogen or an aliphatic radical of 1 to 5 carbon atoms, is reacted with water at a temperature of from 0°–200° C. in the presence of from 0.1 to 50 moles per mole of II of a carboxylic acid of the formula

    III where R has the above meanings.

2. The process of claim 1, wherein the compound of the formula II is 1,1,4-triacetoxy-2-methyl-but-2-ene.

3. The process of claim 1, wherein the carboxylic acid of the formula III is acetic acid.

4. The process of claims 1, 2 or 3 wherein the reaction is carried out at a temperature of 80°–200° C.

5. The process of claims 1, 2 or 3 wherein from 1 to 5 moles of the carboxylic acid per mole of II are used in the process.

* * * * *